United States Patent [19]

Delaage et al.

[11] Patent Number: 5,246,829
[45] Date of Patent: Sep. 21, 1993

[54] PRODUCTS FOR SEPARATION APPLICABLE TO CELLS IN THE IMMUNOPURIFICATION FIELD

[75] Inventors: Michel Delaage; Jean-Louis Drocourt; Jöelle Hirn; Andréas van Agthoven, all of Bouches-du-Rhone, France

[73] Assignee: Immunotech, Marseilles, France

[21] Appl. No.: 848,898

[22] Filed: Mar. 10, 1992

Related U.S. Application Data

[60] Division of Ser. No. 7,251,119, Sep. 29, 1988, Pat. No. 5,116,724, which is a continuation of Ser. No. 6,787,908, Oct. 4, 1985, abandoned.

[30] Foreign Application Priority Data

Oct. 4, 1984 [FR] France ............................. 8415434

[51] Int. Cl.$^5$ .................... C12N 1/00; C12N 11/00
[52] U.S. Cl. .............................. 435/2; 435/30; 435/174; 435/177; 435/180; 435/239; 435/243
[58] Field of Search ............. 435/2, 30, 174, 177, 435/180, 239, 243; 436/533, 534

[56] References Cited

U.S. PATENT DOCUMENTS

| | | | |
|---|---|---|---|
| 3,970,518 | 7/1976 | Giaever | 435/239 |
| 4,035,316 | 7/1977 | Yen et al. | 436/533 X |
| 4,048,298 | 9/1977 | Niswender | 436/533 X |
| 4,264,766 | 4/1981 | Fischer | 436/533 |
| 4,298,689 | 11/1981 | Doyle et al. | 435/34 |
| 4,342,739 | 8/1982 | Kakimi et al. | 436/518 |
| 4,401,764 | 8/1983 | Smith | 436/534 X |
| 4,459,361 | 6/1984 | Gefter | 436/534 X |
| 4,511,662 | 4/1985 | Baran et al. | 436/534 X |
| 4,582,810 | 4/1986 | Rosenstein | 436/532 X |
| 4,590,170 | 5/1986 | Akiyoshi et al. | 436/533 |
| 4,610,962 | 9/1986 | Takaji et al. | 435/180 X |
| 4,650,769 | 3/1987 | Kakimi et al. | 436/533 |
| 4,656,143 | 4/1987 | Baker et al. | 436/534 X |
| 4,721,681 | 1/1988 | Lentrichia et al. | 436/534 X |
| 5,017,472 | 5/1991 | Bankert et al. | 435/7.25 |

FOREIGN PATENT DOCUMENTS

| | | |
|---|---|---|
| 122209 | 10/1984 | European Pat. Off. |
| 50-082230 | 7/1975 | Japan |
| 2027031 | 2/1980 | United Kingdom |
| 2005275 | 4/1980 | United Kingdom |

OTHER PUBLICATIONS

Biological Abstracts, vol. 78, ref. no. 19564, J. Wormmeester et al. "A Simple Method for Immunoselective Cell Separation with the Avidio-Biotin System" and *J. Immunol. Methods* 67(2):389-394 (1984) Abstract.

Molday, "Cell Labelling and Separation Using Immunospecific Microspheres", in Pretlow et al. (Eds.), *Cell Separation*, Academic Press, N.Y., 1984, pp. 237-247.

Wormmeester et al., Biological Abstracts 78, abstr. No. 19564, "A Simple Method for Immunoselective Cell Separation with the Avidio-Biotin System", J. Immunol. Methods, 67(2): 389-394 (1984).

R. Y. Stanier et al., *The Microbial World*, Second Edition, Prentice-Hall, Inc., Englewood Cliffs N.J., 1963, pp. 139-140, 204.

Biological Abstracts, vol. 68, 1979, abstr. No. 67642, J. W. Stocker et al., "Separation of Human Cells Bearing HLA-DR Antigens Using a Monoclonal Antibody Rosetting Method" and Tissue Antigens 3(3): 212-222, 1979.

Biological Abstracts, vol. 76, 1983, ref No. 31400, T. Hoang et al., "Separation of Hemopoietic Cells from Adult Mouse Marrow by Use of Monoclonal Antibodies" and Blood 61(3): 580-588, 1983.

R. J. Doyle et al., *Jour. Clin. Microbiol.*, 19, 383-387, 1984.

I. J. Goldstein, in "Qualityline" Newsletter of Miles Laboratories, Inc., pp. 5-8, Spring 1980.

*Primary Examiner*—David Saunders
*Attorney, Agent, or Firm*—Browdy and Neimark

[57] ABSTRACT

The invention relates to a product to permit separation of cells in the domain of immunopurification and consisting of a finely divided carrier of a density lower than that of the medium from which such cells must be extracted, such carrier being covered with macromolecules capable of being specifically fixed to the cells to be extracted to which a priviliged orientation was given to enable fixation of such macromolecules.

11 Claims, No Drawings

PRODUCTS FOR SEPARATION APPLICABLE TO CELLS IN THE IMMUNOPURIFICATION FIELD

This is a division of application Ser. No. 07/251,119 filed Sep. 29, 1988 and now Pat. No. 5,116,724, which, in turn, was a continuation of application Ser. No. 06/787,968 filed Oct. 2, 1985, now abandoned.

This invention relates to a product for separation of cells or viruses from biological media. It consists of particles which are "floatable", i.e. particles having a density lower than the medium in which they are used, such particles being covered with macromolecules capable of specific fixation (binding) to the cells to be extracted.

It is meant by "cells" in this description bacterias, cells, whether animal or vegetal, and cells obtained by genetic recombination. This invention also applies to other microorganisms and viruses.

Unsoluble carriers used until now in the immunopurification processes are generally particles of "Nylon", glass balls, polystyrene balls, silica gels or gels based on derivatives of cellulose, agarose, acrylamide, dextrane and the like.

When such carriers are presented in form of balls they have however the disadvantage of sedimenting simultaneously with the cells to be separated.

Recently, to remedy such difficulties, magnetic gels have come to light i.e. gels of the same nature as the preceding ones but containing a magnetic charge therein.

Nevertheless such particles are of a high density, depositing quickly and capable sometimes of destroying partly the separated substances such as for example the cells in the cellular purification processes (rupture by mechanical frictions). These gels moreover require the use of apparatus (magnets) to facilitate separation by means of a magnetic field.

Red blood globules have also been used to modify the density of the cells to be separated (see BIOLOGICAL ABSTRACTS, vol. 78, 1984, reference No. 19564, J. WORMMEESTER et al.: "A simple method for immunoselective cell separation with the avidino-biotin system" and J. IMMUNOL. METHODS, 67 (2): 389.394, 1984, as well as BIOLOGICAL ABSTRACTS, vol. 68, 1969, reference No. 67642, J. W. STOCKER et al.: "Separation of human cells bearing HLA-DR antigens using a monoclonal antibody rosetting method", and TISSUE ANTIGENS 3 (3), 212–222, 1979. The red globules however present the following inconveniences:

1) They do not float in biological media but rather only in special solutions (FICOLL's gradient-Metrizoate) where survival of the cells is very precarious;

2) The size of the red globules is of the same order of magnitude than that of the cells to be separated; the complex densities may therefore vary within large limits depending on the number of cells fixed to the globule.

3) The red globule not being in itself an industrial product, it is difficult to stabilize and gives rise to non-specific bonds with certain cells.

Finally, separation of cells using a planar surface, called "panning" permits only analytical utilization.

The object of this invention is a product that does not present the inconveniences mentioned above and provides a low density carrier to which there are fixed antibodies or lectins directed against the substance or substances carried by the cells which are to be separated. The particles used may be of different shapes (balls, sticks, wings, and the like) of variable maximum dimension (from 0.1 to 500 micrometers) and of various nature (polyethylene, polypropylene). For example, they are coated with a macromolecular film according to the process already described in French patent application No. 8305618.

Fixation of the antibody directed against the substance or substances carried by the cells which are to be separated (which will be called "specific antibody") is ensured through the intermediary of a "relay network" (arm) for providing priviliged orientation of the specific antibody relative to that of the antigen carried by the cell.

Among such relay networks, the product according to the invention may result from an avidin-biotined compound system of several alternated layers:

The biotined compound fixing itself to the solid phase is a macromolecule (of the albumin, hemoglobin and the like type) to which several biotin molecules are fixed. Each of the biotin residues may at its turn fix an avidin molecule which avidin having four fixation sites for the biotin is still capable of bonding a second layer of biotined compound etc., the last layer of avidin serving as fixation site for the specific antibody, itself biotined.

According to a modified form of embodiment said orientation can be obtained with an antibody and anti-immunoglobulin system:

In this very case a first antibody is fixed to the solid carrier; such antibody recognizes antibodies of another animal species (rat and anti-mouse); the second specific anti-body of the cells to be purified is then fixed to the first. An advantageous modified form of embodiment consists of using a chain of three antibodies. The anti-antibody antibodies are advantageously directed against the lightweight kappa or lambda chains.

According to still another form of embodiment, the system can be of the antibody and antihaptene type.

In this latter case, the antibody immobilized on the solid phase is an antihaptene antibody, i.e. an antibody directed against a molecule of small molecular weight. The same haptene is moreover bound covalently to the specific antibody intended for purification through a chemical coupling permitting it to be recognized by the antihaptene antibody.

Such system permits purification of antigens and antibody complexes through shifting by means of a free haptene excess.

The following Examples are given by way of illustration and do not at all limit this invention:

EXAMPLE 1

Immobilization to floating avidined balls according to the invention of a monoclonal biotin antibody directed against a cellular surface antigen.

a) For the preparation of avidined floating balls it will be referred to the already mentioned process of patent No. 8305618. It is to be reminded that the material used can be polypropylene or polyethylene of density lower than that of the biological media. The ball diameter is in the order of 50 to 300 micrometers. The fixability of biotin to the avidined balls is evaluated by incubation of radiomarked biotin to 1 nmole/gr of balls.

b) The number of molecules of biotin fixed per molecule of antibody is evaluated by means of 3H biotin-N-hydroxysuccinimide.

There is taken up a monoclonal antibody of mouse (B9-11) directed against the surface antigen T8 specific to a lymphocytic sub-population. Such antibody (1 mg/ml) carrying two molecules of biotin is fixed to avidined balls by incubation at 4° C. for 5 hours in saline solution buffered with phosphate at pH 7.4. The preparation is then washed exhaustively with a socalled preservation solution.

Any loss of balls during the washings and aspirations is avoided by the use of a "Nylon" filter, "Nyltex", then dried at the ambient temperature under controlled hydrometry.

EXAMPLE 2

Immobilization to floating avidined balls of a monoclonal mouse antibody directed against a cellular surface antigen through the intermediary of an arm of a monoclonal, biotined, rat and anti-mouse immunoglobulin, chain K antibody (RAMK).

It is operated as described in Example 1 to fix to the balls the monoclonal RAMK antibody carrying 2 molecules of biotin per molecule. The binding capacity of RAMK balls to antibody B9-11 is estimated by incubation of B9-11 radiomarked to 100 μg/g of balls.

After washing and drying the balls carrying the RAMK, a monoclonal mouse antibody is bound at a concentration of 1 mg/ml by incubation in saline medium buffered by phosphate, pH 7.4, for 16 hours at 4° C.

In the same manner as described in Example 1, the balls are washed and dried for preservation.

EXAMPLE 3

Immobilization to floating avidined balls of a monoclonal mouse antibody directed against a cellular surface antigen through the intermediary of an arm of monoclonal, biotined, mouse anti-rat immunoglobulin, chain K antibody (MARK), plus the monoclonal, rat, anti-mouse immunoglobulin, chain K, antibody (RAMK).

a) It is operated as described in Example 1 for binding to the balls one molecule of antibody MARK carrying 2 molecules of biotin. Such balls-MARK have the capacity of fixing 100 μg of rat antibody per g; such capacity is evaluated by incubation of a radiomarked monoclonal rat antibody.

The balls MARK are incubated with the antibody RAMK at a concentration of 1 mg/ml in saline medium buffered with phosphate, pH 7.4, for 16 hours at 4° C. The bindability of balls-MARK-RAMK to the monoclonal radiomarked mouse antibody B9-11 is evaluated to 2 mg/g of balls.

After washing under the same conditions, the balls-MARK-RAMK are incubated with a monoclonal mouse antibody at a concentration of 1 mg/ml and then again washed and dried for preservation.

b) To fix a monoclonal rat antibody it is proceeded in the same manner but by taking care to exchange the order of fixation of antibodies to the avidined balls.

TESTS IN VITRO

A: Fixation of lymphoblastoidic cells T of the HPBALL line with the different above-mentioned ball systems.

A small quantity of balls (about 1 mg) is incubated with 100 μl of a cellular HPBALL suspension, at $5 \times 10^6$ cells/ml of RPMI. 10% FCS for 20 minutes at the ambient temperature in intermittent stirring.

The balls are washed with a saline solution buffered by phosphate, pH 7.4, and are thereafter observed under optical microscope. The number of visible bound cells per ball is counted.

a) Fixation of the cells by balls carrying B9-11 (Example 1).

b) Fixation of the cells by RAMK-balls carrying B9-11 (Example 2).

c) Fixation of the cells by balls-MARK-RAMK carrying B9-11 (Example 3).

For the three types of balls, a), b) and c), reference balls not carrying the specific antibody do not show any non specific cellular fixation.

In the case of a), 2 to 3 cells per balls are observed.

In the case of b), between 10 and 20 cells per ball are observed, and in the case of c), more than 20 cells per ball are observed.

B: Fixation of the lymphoblastoidic cells T of the HPBALL line with balls-MARK-RAMK carrying different monoclonal mouse anti-lymphocyte T antibodies.

It is operated as described under A.

The scale of following values is established:
− less than one cell fixed per ball
+ between 1 and 4 cells per ball
++ between 4 and 10 cells per ball
+++ between 10 and 20 cells per ball
++++ more than 20 cells per ball.

| List of tested monoclonal antibodies: | | |
|---|---|---|
| Antibody | Specificity | Fixation scale |
| $8H_{8.1}$ | $GP_{41}$ | + |
| $13B_{8.2}$ | $T_4$ | + |
| $6F_{103}$ | $T_{11}$ | + |
| 25.3 | LFA-1 | ++ |
| $B_{9.11}$ | $T_8$ | ++++ |
| $BL_4$ | $T_4$ | ++ |
| $16G_5$ | $T_3$ | ++ |
| $SPL_{14}$ | $T_{12}$ | ++ |
| Leu I | $T_1$ | ++++ |
| $BL_{1a}$ | $T_1$ | − |

C: Fixation of the lymphoblastoidic cells T of the HPBALL line incubated previously with the specific monoclonal mouse antibody and then brought into contact with the balls MARK-RAMK.

100 μl of a cellular HPBALL suspension at $5 \times 10^6$ cells/ml are directly incubated with 20 μg of a monoclonal, antilymphocyte T, mouse antibody. Two washings are effected with the same saline solution to eliminate the excess of antibody and the cells are brought again into suspension in the medium RPMI 10% FCS.

In a second incubation step the cellular suspension is brought at a concentration of $5 \times 10^6$ cells per ml into the presence of 1 g of balls-MARK-RAMK.

With the optical microscope a slight increase in the cellular fixation is observed, especially in the case of negative $BL_1$ during incubation in a single step.

EXAMPLE 4

Elimination of a cellular subpopulation from a lymphocytic preparation of the peripheral blood and a lymphocytic preparation of the bone marrow observed by fluorographic analysis.

Separation of lymphocytes from the peripheral blood and the bone marrow is effected by the technique of density on FICOLL already described by Boyum. A (Scand.J.Clin.Lab.Invest., 2 (Suppl. 97): 77, 1968).

The viability of the cells is checked by Trypan blue exclusion and is estimated to be higher than 95%.

$4 \times 10^6$ cells in 1 ml of RPMI. 10% FCS are incubated with 20 mg of dry MARK-RAMK B9-11 balls for 2 hours at the ambient temperature and under rotary stirring (5 rotations per minute). It is proceeded with identical incubation with reference balls.

Upon completing the incubation, the unreacted cells are recovered by decantation and aspiration by using a "Nyltex" filter. The recovered cells are counted; a decreased cell numbering of between 30 to 50% is observed in case of the treatment with B9-11 as compared to the reference balls.

The recovered lymphocytes are incubated in saline phosphate medium containing 0.2% of bovine albumin with 20 μg of B9-11 for 1 hour at 4° C. After washing, the cells are incubated with a fluorescent goat anti-mouse probe marked with fluoroisothiocyanate and prepared for fluorographic analysis.

The peripheral blood contains 30% of positive cells with antibody B9-11. Treated by the reference balls it keeps them entirely; treated by the balls carrying the antibody B9-11, it loses all the positive cells for such antibody.

The lymphocytes of the bone marrow treated with reference balls having a positivity of 5 to 10% with antibody B9-11 have become negative with B9-11, following the treatment with the balls carrying the B9-11. An antibody against the antigen of acute leukemia (CALLA), $ALB_2$ having a positivity of 15% on this same lymphocytic marrow population is positive at 17% after treatment with the balls B9-11.

EXAMPLE 5

Utilization of the product according to the invention for treating samples of marrow for grafting on.

This is a particularly important application of the product according to the invention. From 10 to 30 g of balls treated as in Examples 2 and 3 carrying an anti-cell T antibody are dried and introduced into a blood transfer pouch of 450 ml. The whole of it is sterilized by exposure to gamma-rays according to the usual protocols. At the time of use the balls are rehumidified by a buffer solution and then the marrow sample previously centrifugated and semi-purified on FICOLL barrier is thereafter introduced, brought into the presence of balls for 2 hours with slow rotation providing contact between the balls and the cells. After decanting, the cells not bound to the balls are injected to the patient for reconstitution of his marrow.

Generally, the product according to the invention finds very large domains of application. In a non-exhaustive manner, the following applications can be cited in case of the cellular sorting, whether it be of the preparative type, as for:

elimination of T cells from grafted marrows,
elimination of fibroblastic cells from cellular cultures;
prepartation of deleukocyted blood using an anti-HLA antibody or an anti-beta-microglobulin;
or the positive separation such as for:
preparation of pancreatic B cells (producing insulin in Langherhans islets);
recovery of cells or microorganisms from contaminated cultures, or, of the analytic type, as for:
the subtractive operations in case of T and B lymphocytes;
lymphocytic T4+ and T8+ subpopulations;
leukemic cells (Galla +) and the like,
or for positive detection (marking of balls after reaction with the cells using a cellular antigen);
or quantification of rare subpopulations, and the like.

There can also be cited the possibility of applying the product of the invention to the concentration, detection, identification of viruses from samples of large volume (for example controlling drinkable waters), purification of biological media.

It will be understood that this invention was only described in a purely illustrative and not at all limitative manner and that any modifications in particular as regards equivalents can be entered therein by the man of the art without however departing from its scope. In particular, certain antibodies can be replaced in the product according to the invention by lectins.

We claim:

1. A product for the extraction of cells or viruses from a biological medium, comprising beads, having a size between 50 and 500 micrometers, said beads having a density lower than unity and being coated with antibodies capable of antigenic binding to cells or viruses to be extracted from the binding of medium, said antibodies being oriented so as to permit binding of said cells or viruses thereto, and said beads being capable of floating upon the surface of the biological medium when antigenically bound to said cells or viruses to be extracted.

2. A product for the extraction of cells or viruses from a biological medium, comprising beads, having a size between 50 and 500 micrometers, and being coated with a substance capable of specifically binding to the cells or viruses to be extracted, said beads having a size and density sufficient to permit the beads to float upon the surface of the biological medium in which the product is to be used when bound to the cells or viruses to be extracted.

3. A product in accordance with claim 2 wherein said substance capable of specifically binding to the cells or viruses is a lectin.

4. A product in accordance with claim 2 wherein said substance capable of specifically binding to the cells or viruses comprises an antibody specific to an antigen on the cells or viruses.

5. A product in accordance with claim 4 wherein said antibody is a monoclonal antibody.

6. A product in accordance with claim 2 wherein said beads comprise polyethylene or polypropylene.

7. A product in accordance with claim 2 wherein said substance is coated on said beads by means of an avidin-biotin compound system of several alternating layers.

8. A product in accordance with claim 4 wherein said antibody is coated on said beads by means of a second antibody, bound to said beads, specific to a lightweight chain of said antibody specific to the cell or virus antigen.

9. A product in accordance with claim 8, wherein said second antibody is bound to said beads by means of a third antibody, bound to said beads, specific to a lightweight chain of said second antibody.

10. A product in accordance with claim 4 wherein said antibody is coated on said beads by means of an antibody-hapten system in which a second antibody specific to a hapten is bound to said beads and said antibody specific to a cell or virus antigen is covalently bound to a hapten to which said second antibody is specific.

11. A product in accordance with claim 4 wherein said antibody is specific for a human leukocyte subpopulation.

* * * * *